US006280778B1

(12) United States Patent
Gaudet et al.

(10) Patent No.: US 6,280,778 B1
(45) Date of Patent: Aug. 28, 2001

(54) PROCESS FOR PREPARING NATURAL PRODUCT DERIVATIVES FROM PLANTS IN A SINGLE STEP

(76) Inventors: Daniel Gaudet, 315 rue Chabanel, Chicoutimi, Québec (CA), G7H 3S1; André Pichette, 180 rue du Cran, Chicoutimi, Québec (CA), G7J 2K2

( * ) Notice: Subject to any disclaimer, the term of this patent is extended or adjusted under 35 U.S.C. 154(b) by 0 days.

(21) Appl. No.: 09/431,848

(22) Filed: Nov. 2, 1999

(30) Foreign Application Priority Data

Nov. 2, 1998 (CA) .................................................. 2250481

(51) Int. Cl.[7] .......................... A61K 35/78; A61K 31/19; A61K 31/56

(52) U.S. Cl. .......................... 424/769; 424/725; 424/765; 514/169; 514/557; 514/570; 514/572; 514/573; 514/661

(58) Field of Search ................................ 424/195.1, 769, 424/775, 725; 514/169, 557, 570, 572, 573, 661

(56) References Cited

U.S. PATENT DOCUMENTS 5,171,570 * 12/1992 Takemori et al. ................ 424/195.1
5,804,575 * 9/1998 Pezzuto et al. ...................... 514/169

FOREIGN PATENT DOCUMENTS

2187320 * 2/1974 (FR) .
5201843 * 8/1993 (JP) .
2571201 * 1/1997 (JP) .
410139601 * 5/1998 (JP) .

* cited by examiner

*Primary Examiner*—Christopher R. Tate
(74) *Attorney, Agent, or Firm*—Kramer Levin Naftalis & Frankel, LLP.

(57) ABSTRACT

A process is disclosed, for preparing a derivative of a targeted natural product from plants. The targeted natural product is extracted from the desired part of the plant and the targeted natural product is transformed into the desired derivative(s). Both the extraction and transformation are carried out in a single step consisting of macerating the desired part of the plant into a composition comprising an organic solvent and a reactive agent. This process is particularly useful for preparing derivatives of betulin or lupeol from bark of birch.

21 Claims, 2 Drawing Sheets

PROCESS FOR PREPARING NATURAL PRODUCT DERIVATIVES FROM PLANTS IN A SINGLE STEP

FIELD OF THE INVENTION

The present invention relates to a process for preparing derivatives of targeted natural product from a desired part of a plant in one step. This process is characterized in that the extraction of the targeted natural product from the desired part of the plant and the transformation of the targeted natural product into the desired derivative(s) thereof are carried out in a single step.

BACKGROUND

It has been well established that the outer bark of most white-barked birch, such as Betula papyrifera Marsh. species, are rich in pentacyclic triterpenoid compounds, particulary betulin. Betulin and other natural triterpenoids have been extracted in good yields (20 to 30% of dry weight) from the bark of birch with organic solvents. The betulin is the major triterpenoid compound in the bark of white birches and represents about 70% of the total triterpene.

The major interest in betulin lies in the fact that it is a synthetic precursor of triterpenoid compounds having important pharmacological properties. To obtain these triterpenoid compounds, betulin must be subjected to some chemical reactions. This approach involves a step of purification of the extracted betulin and one or more steps of chemical reactions to produce the desired compound. These reactions are often non-quantitative (yield inferior to 100%) and an additional step of purification is necessary after each chemical reaction. This approach generally provides a low yield of triterpenoid compounds.

SUMMARY OF THE INVENTION

The object of the invention is to provide a process for preparing one or more natural product derivatives which is less time-consuming and/or gives a higher yield than the known processes.

More particularly, the object of the invention is to provide a process for preparing a derivative of a targeted natural product by extraction of the targeted natural product from a desired part of a plant and transformation of the so-extracted targeted natural product into said derivative, wherein the extraction and transformation are carried out in a single step consisting of macerating the desired part of the plant in a composition comprising:

an organic solvent; and a reactive agent.

According to a preferred embodiment of the invention, the process is used for preparing a derivative of betulin by extraction of betulin from bark of white birch and transformation of the so-extracted betulin into a derivative thereof, wherein the extraction and transformation are carried out in a single step consisting of macerating the bark of white birch in a composition comprising:

an organic solvent; and a oxidative agent.

The invention and its advantages will be better understood upon reading the non-restrictive description of a preferred embodiment thereof, made with reference to the appended drawings.

DETAILED DESCRIPTION OF THE INVENTION

As aforesaid, the present invention is concerned with a process for preparing a derivative of a targeted natural product by extraction of the targeted natural product from a desired part of a plant and transformation of the so-extracted targeted natural product into said derivative. The extraction and transformation are carried out in a single step consisting of macerating the desired part of the plant in a composition comprising an organic solvent and a reactive agent.

Barks of birch are preferably used in the process, since they contain a plurality of interesting natural products. Of course, other parts and other plants can be used in the process of the invention.

Barks of white birch (*Betula papyrifera* Marsh) are preferably used in the present invention since they present a high content of betulin therein and its important bioavailability in the southern area of the province of Quebec in Canada. Other kinds of birch can also be used, such as the yellow birch (*Betula alleghaniensis*) which contains an appreciable amount of lupeol therein. However, different types of birch can be used such as the following ones: *Betula papyrifera* Marsh (white birch), *Betula verrucosa* (white birch), *Betula pubescens* (white birch), *Betula populifolia* Marsh. (gray birch), *Betula cordifolia* Regel. (mountain paper birch), *Betula X caerulea* Blanch. (blue birch), *Betula alleghaniensis* (yellow birch) and *Betula platyphylla* var. *japonica*. The type of birch listed in Hayer, E. W. H. et al., Phytochemistry, Vol. 28, No. 9, pp. 2229–2242, 1989, can also be used in the process of the invention.

The process can be advantageously used for preparing a derivative of betulin or a derivative of lupeol. It should be understood that the invention is not limited to betulin and lupeol as targeted natural products.

The organic solvent is preferably selected from the group consisting of chloroform ($CHCl_3$), dichloromethane ($CH_2Cl_2$), diethyl ether ($(CH_3CH_2)_2O$), tetrahydrofurane, acetone, pyridine and dimethylformamide (DMF).

Figure 1:
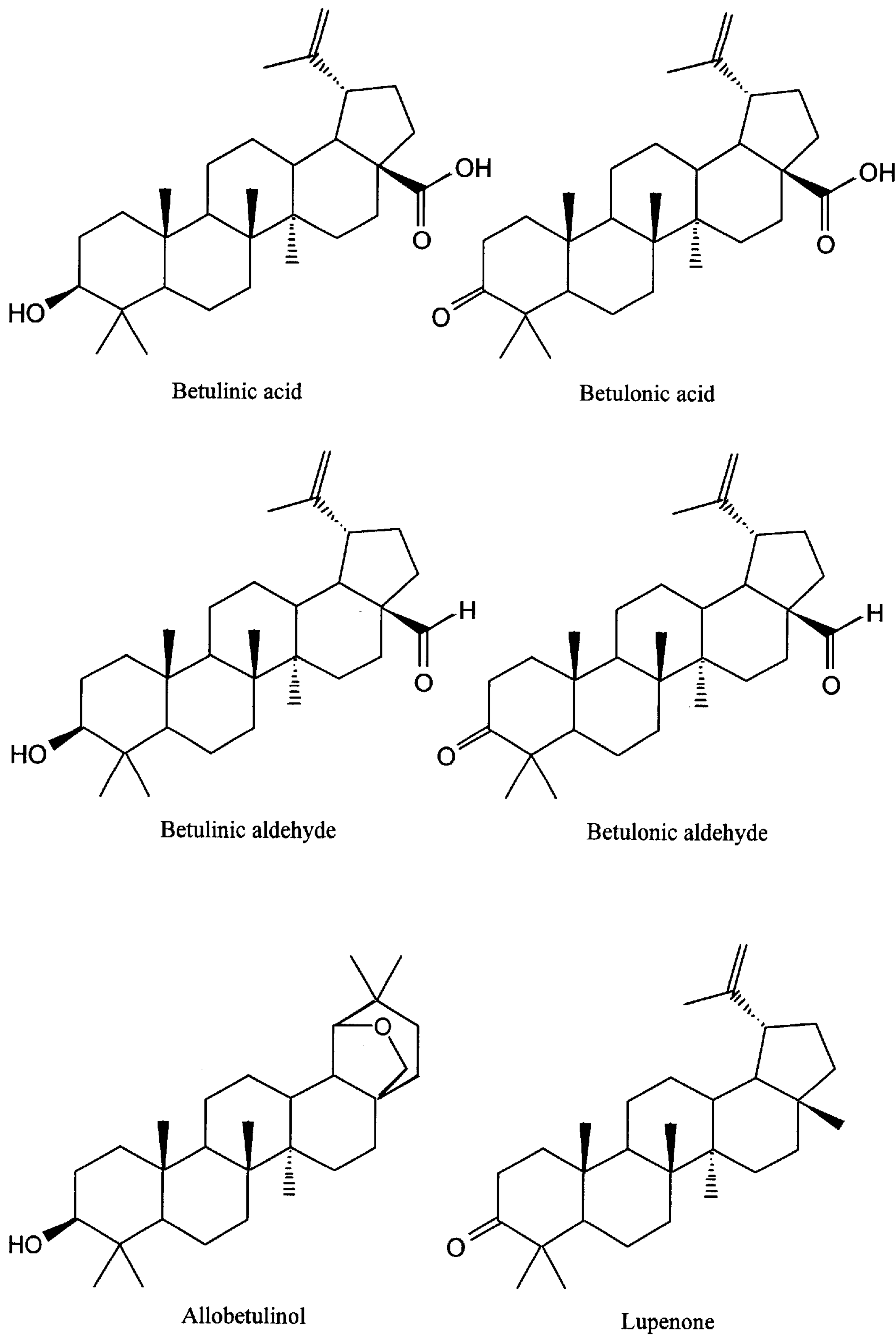
FIG. 1 shows five derivatives of betulin and one derivative of lupeol.
Figure 2:
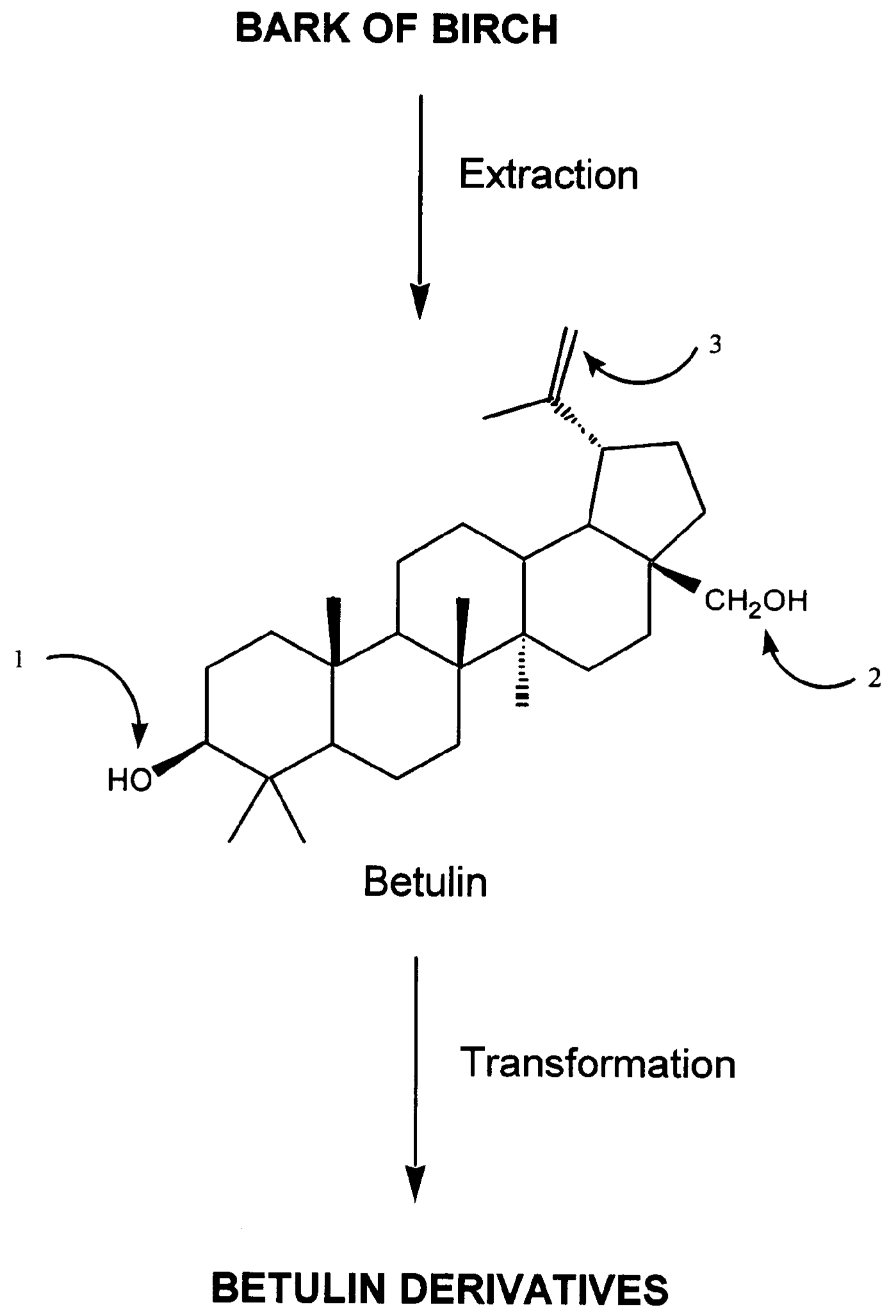
FIG. 2 is a schema of the process according to a preferred embodiment of the invention where the molecular structure of betulin is shown.

According to a preferred embodiment of the invention, the betulin is targeted and the following derivatives can be prepared at different yields: allobetulin, betulinic aldehyde, betulonic aldehyde, betulinic acid and betulonic acid which are illustrated in FIG. 1. Other derivatives can also be prepared by the process of this preferred embodiment such as betulone. Preferably, the derivatives of betulin prepared by the process are comprised in a group of the triterpenoid compounds including those mentioned above. This preferred embodiment of the invention is schematized in FIG. 2.

According to another preferred embodiment of the invention, lupeol is targeted and the prepared derivative thereof is lupenone.

Different reactive agents can be used in the invention, and the necessary one to prepare the above mentioned derivatives of betulin and derivatives of lupeol is an oxidative agent.

Preferably, the oxidative agent is selected from the group consisting of iron nitrate ($(FeNO_3)_3.9H_2O$), copper nitrate ($Cu(NO_3)_2.2,5\ H_2O$), chromium nitrate ($Cr(NO_3)_3.9H_2O$), zinc nitrate ($Zn(NO_3)_2.6H_2O$), mercury nitrate ($Hg(NO_3)_2.H_2O$), cerium nitrate ($Ce(NO_3)_3.6H_2O$), manganese nitrate ($Mn(NO_3)_2.6H_2O$), silver nitrate ($AgNO_3$), chromium oxide ($CrO_3$), ferric chloride ($FeCl_3.6H_2O$), silver chloride ($AgCl_3$), Jone's reagent, pyridinium chlorochromate (PCC), pyridinium dichromate (PDC), chromia-pillared montmorillonite catalyst (Cr-PILC), potassium ferrate ($K_2FeO_4$), potassium manganate ($K_2MnO_4$), potassium permanganate ($KMnO_4$), barium manganate ($BaMnO_4$), silver carbonate ($Ag_2CO_3$), ruthenium chloride ($RuCl_3$) and 2,2,6,6-tetramethylpiperidinyl-1-oxy (TEMPO).

Depending on which oxidative agent or combination of oxidative agents is present in the organic solvent, the identity and the yield of the desired derivative or derivatives may vary. Generally, only one oxidative agent is used but a combination of two or more oxidative agents can be used in the process of the invention.

Preferably, the oxidative agents are adsorbed onto a solid support prior to carrying out the extraction and transformation step. The solid support may be silica gel, alumina, montmorillonite K-10 or other solid supports. However, the Jone's reagent and the PCC are preferably not adsorbed prior to being used in the process.

In accordance with the invention, the maceration of the process is preferably carried out at a temperature of from −80° C. to 160° C. and, more particularly, from −5° C. to 50° C. Also preferably, the maceration is carried out for a period varying between 1 minute and 24 hours. By varying the time of maceration, one can modulate the identity of the derivative prepared by the process. Preferred intervals of temperature and time have been determined with respect to the preferred organic solvents and the preferred oxidative agents listed above. However, it is to be understood that the maceration can be carried out at a temperature and for a period of time different from the ones described above without departing from the scope of the invention.

Also according to the invention, the maceration of the process may be carried out under the ambient air or an inert gas such as nitrogen, argon or helium and possibly in the presence of oxygen in order to modulate the identity of the desired derivatives prepared by the process or to optimize the resulting yield of the desired natural product derivative.

In practice, one or more desired derivatives may be prepared by the process at the same time. For example, using the bark of white birch, the process can used to prepare betulinic aldehyde and betulonic aldehyde at the same time.

According to a preferred embodiment of the invention, the solution resulting from the process of extraction and transformation can be subjected to an additional treatment with the reactive agent. More particularly, the remaining solution containing the organic solvent and all the soluble components contained therein can be isolated from the residual parts of the plant and an additional amount of a reactive agent can be added to the remaining solution in order to obtain a desired derivative. Such additional treatment is exemplified in Example 4.

In use, the extraction and transformation step of the process is preferably followed by a step of purification of the desired derivative or derivatives of betulin. The purification may be achieved by precipitation, recrystallization, flash chromatography on silica gel or any other techniques of purification.

EXAMPLE 1

Preparation of Betulonic Aldehyde 1.00 g of bark of white birch (*Betula papyrifera* Marsh) and 1.02 g of chromium oxyde being adsorbed on silica gel ($CrO_3/SiO_2$, 1:4) are deposited in 60 ml of chloroform at room temperature. The heterogeneous solution is agitated during 100 minutes and then the residual bark and silica gel are removed from the maceration medium by filtration. In order to minimise the loss of products, the residual bark and silica gel are rinsed with 2 or 3 batches of 20 ml of chloroform. The chloroform recovered from the maceration and the rinse steps is distilled by evaporation under vacuum and an oil is so obtained. This oil is submitted to flash chromatography on silica gel using dichloromethane. The less polar and more abundant product ($R_f$=0.68, 2% $CH_3OH/CH_2Cl_2$ on silica gel) is recovered in the first fractions. After evaporating the solvent from the first fractions, a white solid is obtained which corresponds to a total extraction-transformation yield of 5.9% of betulonic aldehyde. The analysis by capillary gas chromatography of these first fractions shows that the level of purity of the desired recovered product is higher than 95%. The identity of the recovered product is determined by proton nuclear magnetic resonance ($^1H$ NMR) and by mass spectrometry (MS). The identity is confirmed by comparing the obtained spectroscopic results to the published data in Hua, Y. et al., J. of Wood Chem. and Tech. 11:503–517 (1991).

$^1H$ NMR ($CDCl_3$, 300 MHz, δ in ppm): 9.67 (d, J=2 Hz, 1 H, 28-H), 4.76 (m, 1 H, 29-H), 4.64 (m, 1 H, 29-H), 2.87 (m, 1 H, 19-H), 2.45 (m, 2 H, 2-H), 1.70 (s, 3 H, 30-$CH_3$), 0.93, 0.96, 0.99, 1.02, 1.07 (all singlets, 15 H, 5×$CH_3$).

EI-MS: 438 (M, 6), 55 (100), 81 (83), 41 (80), 67 (73), 79 (72), 69 (70), 93 (68), 95 (68), 107 (66), 91 (65), 43 (64).

EXAMPLE 2

Preparation of Betulinic Aldehyde 1.00 g of bark of white birch (*Betula papyrifera* Marsh) and 0.68 g of chromium oxyde being adsorbed on silica gel ($CrO_3/SiO_2$, 1:4) are deposited in 50 ml of chloroform at room temperature. The heterogeneous solution is agitated for a period of 20 minutes and then the residual bark and silica gel are removed from the maceration medium by filtration. In order to minimize the loss of products, the residual bark and silica gel are rinsed with 2 or 3 batches of 20 ml of chloroform. The chloroform recovered from the maceration and the rinse steps is distilled by evaporation under vacuum and the oil that is so obtained is submitted to flash chromatography on silica gel using dichloromethane. The fractions containing the second less polar product of the extracted oil ($R_f$=0.38, 2% $CH_3OH/CH_2Cl_2$ on silica gel) are combined. After evaporating the solvent from these fractions, a white solid is obtained which corresponds to a total extraction-transformation yield of 3.7%. The analysis by capillary gas chromatography of these fractions shows that the level of purity of the desired recovered product is higher than 95%. The identity of the recovered product is determined by proton nuclear magnetic resonance ($^1H$ NMR) and by mass spectrometry (MS). The identity is confirmed by comparing the obtained spectroscopic results to the published data in Pathak, N. K. R. et al., Indian J. Pharm. Sci., Vol. 30, pp.124–125.

$^1H$ NMR ($CDCl_3$, 300 MHz): δ 9.68 (d, J=1 Hz, 1 H, 28-H), 4.75 (m, 1 H, 29-H), 4.63 (m, 1 H, 29-H), 3.17 (m, 1 H, 3-H), 2.87 (m, 1 H, 19-H), 1.00–2.10 (complexe, $CH_2$, CH), 1.70 (s, 3 H, 30-$CH_3$), 0.75, 0.82, 0.92, 0.96, 0.98 (all singlets, 15 H, 5×$CH_3$).

EI-MS: 440 ($M^+$, 7), 43 (100), 55 (97), 81 (96), 189 (96), 95 (89), 69 (86), 41 (85), 93 (84), 135 (80), 67 (78), 107 (78).

EXAMPLE 3

Preparation of Allobetulin 1.01 g of bark of white birch (*Betula papyrifera* Marsh) and 0.40 g of iron chloride being adsorbed on silica gel ($FeCl_3/SiO_2$, 1:4) are deposited in 50 ml of dichloromethane at room temperature. The heterogeneous solution is agitated for 20 minutes and then the residual bark and the silica gel are removed from the maceration medium by filtration. In order to minimize the loss of products, the residual bark and silica gel are rinsed with 2 or 3 batches of 20 ml of chloroform. The chloroform and the dichloromethane recovered from the maceration and the rinse steps are distilled by evaporation under vacuum and an oil is so obtained which is submitted to flash chromatography on silica gel using dichloromethane. The fractions containing the second less polar product from the extracted oil ($R_f$=0.25, 1% $CH_3OH$ in $CH_2Cl_2$ on silica gel) are combined. After evaporating the solvent from these fractions, a white solid is obtained which corresponds to an extraction-transformation yield of 11.9%. The analysis by capillary gas chromatography of these fractions shows that the level of purity of the desired recovered product is higher than 95%. The identity of the recovered product is determined by proton nuclear magnetic resonance ($^1$H NMR) and by mass spectrometry (MS). The identity is confirmed by comparing the obtained spectroscopic results to the published data in Lugemwa, F. N. et al., J. Agric. Food Chem. 38:493–496 (1990).

$^1$H NMR ($CDCl_3$, 300 MHz): δ 3.76 (d, J=8 Hz, 1 H, 28-H), 3.52 (s, 1 H, 19-H), 3.42 (d, J=8 Hz, 1 H, 28 H), 3.20 (m, 1 H, 3-H), 1.01–1.78 (complexe, $CH_2$, CH), 0.96, 0.92, 0.91, 0.83, 0.78, 0.75, (all singlets, 21 H, 7×$CH_3$).

EI-MS: 442 ($M^+$, 14), 107 (100), 189 (95), 135 (79), 121 (78), 207 (58), 203 (35), 220 (16), 424 (13), 371 (9), 411 (7).

EXAMPLE 4

Preparation of Betulinic Acid 5.00 g of bark of white birch (*Betula papyrifera* Marsh) and 11.3 g chromium oxyde being adsorbed on alumina ($CrO_3/Al_2O_3$ 1:4) are deposited in 100 ml of dichloromethane at room temperature. The heterogeneous solution is agitated for 20 minutes and then the residual bark and alumina are removed from the maceration medium by filtration. In order to minimize the loss of products, the residual bark and alumina are rinsed with 2 or 3 batches of 50 ml of chloroform. The chloroform and the dichloromethane recovered from the maceration and the rinse steps are distilled by evaporation under vacuum and a white powder is obtained. This powder is dissolved in 100 ml of acetone and 0.67 g of potassium permanganate are added thereto. The resulting solution is agitated at room temperature for 1 hour. Then, 200 ml of water are added to the solution and the aqueous phase is extracted 3 times with 60 ml of dichloromethane. The organic phase is washed with 3 batches of 50 ml of water, dried with anhydrous $MgSO_4$ and then filtrated by gravity. The so resulting solution is concentrated and submitted to flash chromatography on silica gel using dichloromethane and methanol (1% methanol/dichloromethane). The identity of the betulinic acid is confirmed by comparison of mass spectra of methyl ester derivates with authentic samples from Aldrich®.

Although a preferred embodiment of the invention has been described in detail herein and illustrated in the accompanying drawings, and only four examples have been given, it is to be understood that the invention is not limited to this preferred embodiment and examples, and that various changes and modifications could be made without departing from the scope or spirit of the invention.

What is claimed is:

1. A process for preparing a derivative of a targeted natural product selected from the group consisting of betulin or lupeol, the process comprising a single step of:

macerating a desired part of a plant known to contain the targeted natural product into a composition comprising:

an organic solvent causing extraction of the targeted natural product from the desired part of the plant; and a reactive agent causing transformation of the extracted natural product into said derivative, said transformation being an oxidation or a rearrangement.

2. A process as claimed in claim 1, wherein the plant is a birch and the part thereof is a bark.

3. A process as claimed in claim 2, wherein the birch is selected from the group consisting of *Betula papyrifera* Marsh (white birch), *Betula verrucosa* (white birch), *Betula pubescens* (white birch), *Betula populifolia* Marsh. (gray birch), *Betula cordifolia* Regel. (mountain paper birch), *Betula X caerulea* Blanch. (blue birch), *Betula alleghaniensis* (yellow birch) and *Betula platyphylla* var. *japonica.*

4. A process as claimed in claim 1, wherein the organic solvent is selected from the group consisting of chloroform ($CHCl_3$), dichloromethane ($CH_2Cl_2$), diethyl ether ($(CH_3CH_2)_2O$),tetrahydrofurane, acetone, pyridine and dimethylformamide (DMF).

5. A process as claimed in claim 4, wherein the reactive agent is an oxidative agent.

6. A process as claimed in claim 5, wherein the oxidative agent is selected from the group consisting of iron nitrate ($(FeNO_3)_3.9H_2O$), copper nitrate ($Cu(NO_3)_2.2,5H_2O$), chromium nitrate ($Cr(NO_3)_3.9H_2O$), zinc nitrate ($Zn(NO_3)$ $2.6H_2O$), mecury nitrate ($Hg(NO_3)_2.H_2O$, cerium nitrate ($Ce(NO_3)_3.6H_2O$), manganese nitrate ($Mn(NO_3)_2.6H_2O$), silver nitrate ($AgNo_3$), chromium oxide ($CrO_3$), ferric chloride ($FeCl_3.6H_2O$), silver chloride ($AgCl_3$), Jone's reagent, pyridinium chlorochromate (PCC), pyridinium dichromate (PDC), chromia-pillared montmorillonite catalyst (Cr-PILC), potassium ferrate ($K_2FeO_4$), potassium manganate ($K_2MnO_4$), potassium permanganate ($KMnO_4$), barium managanate ($BaMnO_4$), silver carbonate ($Ag_2CO_3$), ruthenium chloride ($RuCl_3$) and 2,2,6,6-tetramethylpiperidinyl-1-oxy (TEMPO).

7. A process as claimed in claim 5, wherein, the oxidative agent is adsorbed onto a solid support, and the oxidative agent is selected from the group consisting of iron nitrate ($(FeNO_3)_3.9H_2O$), copper nitrate ($((Cu(NO_3)_2.xH_2O)$, chromium nitrate ($Cr(NO_3)_3.9H_2$), zinc nitrate ($Zn(NO_3)_2.6H_2O$), mercury nitrate ($Hg(NO_3)_2.H_2O$), cerium nitrate ($Ce(NO_3)_3.6H_2O$), manganese nitrate ($Mn(NO_3)_2.xH_2O$), silver nitrate ($AgNO_3$), chromium oxide ($CrO_3$), ferric chloride ($FeCl_3.6H_2O$), silver chloride ($AgCl_3$), pyridinium chlorochromate (PCC), pyridinium dichromate (PDC), chromia-pillared montmorillonite catalyst (Cr-PILC), potassium ferrate ($K_2FeO_4$), potassium manganate ($K_2MnO_4$), potassium permanganate ($KMnO_4$), barium manganate ($BaMnO_4$), silver carbonate ($Ag_2CO_3$), and ruthenium chloride ($RuCl_3$).

8. A process as claimed in claim 7, wherein the solid support is silica gel, alumina or montmorillonite K-10.

9. A process as claimed in claim 4, wherein the maceration is carried out at a temperature from −80° C. to 160° C.

10. A process as claimed in claim 6, wherein the maceration is carried out under ambient air or an inert gas.

11. A process as claimed in claim 10, wherein the inert gas is selected from the group consisting of nitrogen, argon and helium.

12. A process as claimed in claim 10, wherein the maceration is carried out in the presence of oxygen.

13. A process as claimed in claim 6, wherein the maceration is carried out for one minute to 24 hours.

14. A process as claimed in claim 1, wherein the maceration step is followed by a step of purification of the derivative of the targeted natural product.

15. A process as claimed in claim 1, wherein the targeted natural product is betulin and the derivative of betulin is selected from the group consisting of allobetulin, betulinic aldehyde, betulonic aldehyde, betulinic acid and betulonic acid.

16. A process as claimed in claim 15, wherein the plant is *Betula papyrifera* Marsh (white birch).

17. A process as claimed in claim 1, wherein the targeted natural product is lupeol and the derivative of lupeol is lupenone.

18. A process as claimed in claim 17, wherein the plant is *Betula alleghaniensis* (yellow birch).

19. A process as claimed in claim 1, wherein the reactive agent is selected from the group consisting of iron nitrate ($(FeNO_3)_3.9H_2O$), copper nitrate ($Cu(NO_3)_2.2,5H_2O$), chromium nitrate ($Cr(NO_3)_3.9H_2O$), zinc nitrate ($Zn(NO_3)_2.6H_2O$), mercury nitrate ($Hg(NO_3)_2.H_2O$), cerium nitrate ($Ce(NO_3)_3.6H_2O$), manganese nitrate ($Mn(NO_3)_2.6H_2O$), silver nitrate ($AgNO_3$), chromium oxide ($CrO_3$), ferric chloride ($FeCl_3.6H_2O$), silver chloride ($AgCl_3$), Jone's reagent, pyridinium chlorochromate (PCC), pyridinium dichromate (PDC), chromia-pillared montmorillonite catalyst (Cr-PILC), potassium ferrate ($K_2FeO_4$), potassium manganate ($K_2MnO_4$), potassium permanganate ($KMnO_4$), barium manganate ($BaMnO_4$), silver carbonate ($Ag_2CO_3$), ruthenium chloride ($RuCl_3$) and 2,2,6,6-tetramethylpiperidinyl-1-oxy (TEMPO).

20. A process as claimed in claim 1, the reactive agent is adsorbed onto a solid support, and the reactive agent is selected from the group consisting of iron nitrate ($(FeNO_3)_3.9H_2O$), copper nitrate ($Cu(NO_3)_2.xH_2O$), chromium nitrate ($Cr(NO_3)_3.9H_2O$), zinc nitrate ($Zn(NO_3)_2.6H_2O$), mercury nitrate ($Hg(NO_3)_2.H_2O$), cerium nitrate ($Ce(NO_3)_3.6H_2O$), manganese nitrate ($Mn(NO_3)_2.xH_2O$), silver nitrate ($AgNO_3$), chromium oxide ($CrO_3$), ferric chloride ($FeCl_3.6H_2O$), silver chloride ($AgCl_3$), pyridinium chlorochromate (PCC), pyridinium dichromate (PDC), chromia-pillared montmorillonite catalyst (Cr-PILC), potassium ferrate ($K_2FeO_4$), potassium manganate ($K_2MnO_4$), potassium permanganate ($KMnO_4$), barium manganate ($BaMnO_4$), silver carbonate ($Ag_2CO_3$), and ruthenium chloride ($RuCl_3$).

21. A process for preparing a derivative of betulin, the process comprising a single step of:

macerating a bark of *Betula papyrifera* Marsh (white birch) in a composition comprising:

- an organic solvent causing extraction of betulin from said bark of white birch; and
- a reactive agent causing transformation of the betulin into said derivative, said transformation being an oxidation or a rearrangement;

wherein the derivative of betulin is selected from the group of allobetulin, betulinic aldehyde, betulonic aldehyde, betulinic acid and betulonic acid.

* * * * *